US005798229A

United States Patent [19]
Strittmatter et al.

[11] Patent Number: 5,798,229
[45] Date of Patent: Aug. 25, 1998

[54] BISPECIFIC MOLECULES RECOGNIZING LYMPHOCYTE ANTIGEN CD2 AND TUMOR ANTIGENS

[75] Inventors: Wolfgang Strittmatter, Ober-Ramstadt; Carlota-Silvia Jäggle, Darmstadt; Stefan Meuer, Heidelberg; Burkhart Shraven, Heidelberg; Martin Wild, Heidelberg, all of Germany

[73] Assignee: Merck Patent Gesellschaft mit beschrankter Haftung, Darmstadt, Germany

[21] Appl. No.: 284,947

[22] Filed: Aug. 2, 1994

[30] Foreign Application Priority Data

Aug. 2, 1993 [EP] European Pat. Off. ............. 93112330

[51] Int. Cl.$^6$ .................. C12P 21/08; C07K 16/28; C07K 16/30; C07K 16/00
[52] U.S. Cl. ..................... 435/70.21; 530/387.3; 530/388.2; 530/388.22; 530/388.75; 530/388.23; 530/388.8; 530/388.85
[58] Field of Search ............... 530/387.3, 388.2, 530/388.22, 388.75, 388.8, 388.85; 424/136.1; 435/70.21

[56] References Cited

FOREIGN PATENT DOCUMENTS

| 0 260 880 | 3/1988 | European Pat. Off. |
| 0 294 703 | 12/1988 | European Pat. Off. |
| 91/03493 | 3/1991 | WIPO |
| 9215683 | 9/1992 | WIPO |

OTHER PUBLICATIONS

Scllom, J., Molecular Foundations of Oncology, ed Samuel Broder, Chapter 6, pp. 95–134, 1991.
Petersen, A. et al., Nature, 329: 842–846, Oct. 29, 1987.
Thurin, J. et al, Cancer Research, 47:1229–1233, Mar. 1, 1987.
Reinder L. H. Bolhuis, Els Sturm, and Eric Braakman, Dept. of Immunology, Dr. Daniel den Hoed Cancer Center, Rotterdam, The Netherlands, "T Cell Targeting in Cancer Therapy", *Cancer Immunology Immunotherapy*, Springer-Verlag 1991, pp. 1–8.
"Letters to Nature", *Nature*, vol. 314, 18 Apr. 1985, pp. 628–633.
Tutt, et al., The Journal of Immunology, "*Trispecific F(ab')$_3$ Derivatives that use Cooperative Signaling via the TCR/ CD2 Complex and CD2 to Activate and Redirect Resting Cytotoxic T Cells*", vol. 147, No. 1, Jul. 1, 1991, pp. 60–69.
M. Wild, et al., Immunobiology, "*T Cell Targeting by Anti–CD2 X Anti–EGR–R Bispecific Antibodies*", vol. 189, No. 1–2, Sep. 30, 1993, p. 165, abstract K.25.
C. Jaggle, et al., Immunobiology, "*Bispecific Antibodies of Targeted Cellular Cytotoxicity*", vol. 189, No. 1–2, Sep. 30, 1993, pp. 155–156, abstract K.9.
H. Bernhard, et al., International Journal of Cancer, "*Induction of Tumor–Cell Lysis by Bi–Specific Antibody Recognizing Ganglioside GD2 and T–cell Antigen CD3*", vol. 55, No. 3, Sep. 30, 1993, pp. 465–470.

*Primary Examiner*—Susan R. Loring
*Attorney, Agent, or Firm*—Millen, White, Zelano, & Branigan, P.C.

[57] ABSTRACT

The present invention relates to novel and highly effective bispecific antibody fragments which recognize lymphocyte CD2 antigen and any variable tumor antigen. Moreover, the invention relates to two new monoclonal antibodies terms AICD2.M1 and AICD2.M2. A combination of these antibodies, whereby at least one of them is a bispecific antibody fragment, can be used successfully in tumor therapy and diagnostics.

17 Claims, 7 Drawing Sheets

BISPECIFIC MOLECULES RECOGNIZING LYMPHOCYTE ANTIGEN CD2 AND TUMOR ANTIGENS

BACKGROUND OF THE INVENTION

The present invention relates to novel bispecific antibody fragments which recognize lymphocyte CD2 antigen and any variable tumor antigen.

Preferably, the antigenic determinant of the epidermal growth factor-receptor (EGF-R) is used as tumor antigen. Moreover, the invention relates to two new monoclonal antibodies termed AICD2.M1 and AICD2.M2, and a combined positive effect of them on tumor lysis, whereby at least one of them is a bispecific antibody fragment. The antibodies and antibody fragments can be used successfully in tumor therapy and diagnostics.

T-lymphocytes are probably the most efficient components of the immune system when tumor cells are to be eliminated. However, most cancer patients do not have significant numbers of cytotoxic T-lymphocytes (CTLs) specifically reactive to their tumor cells (e.g., Knuth et al., Proc. Nat'l Acad. Sci. (USA), 81:3511 (1984)). In order to activate the fully lytic potential of CTLs, these cells have to be directed toward tumor cells for which they have no natural specificity. T-cells can be activated to proliferation, cytokine secretion and cytolytic activity by binding of monoclonal antibodies to certain membrane antigens on the surface of these cells.

Bispecific antibodies (BAb) recognizing tumor-associated antigens with one binding arm and T-cell markers with the other one have been shown to bridge monospecific CTLs and malignant cells (e.g., Staerz et al., Nature, 314:628 (1985)).

T-cell activation by these artificial antibodies may occur through the T-cell receptor (TCR)/CD3 complex, in which the TCR is responsible for the antigen recognition and the CD3 epitope for the transduction of signals generated by the TCR-antigen interaction (e.g., see review article of H. Nelson, Cancer Cells, 163 (May 1991), and references cited therein).

Effector cell activation may also occur via the CD2 antigen, a glycoprotein which is present on T-lymphocytes and natural killer (NK) cells (e.g., Hünig et al., Nature, 326:298 (1987)). CD2 supports the interaction of the effector cell with the natural ligand LFA3 (CD58) on the target cell. Three functionally important epitopes (T11.1, T11.2 and T11.3) have been identified on CD2. In contrast to the CD3 antigen, which undergoes modulation upon antibody binding ,there is no report so far on CD2 modulation after targeting of CD2 with antibody. Earlier work using anti-CD2 antibody for activation has shown that a two-step activation via the CD2 antigen seems realistic. Synergistically-acting anti-CD2-specificities that have been used for activation so far are characterized by antibodies such as anti-T11.2 plus anti-T11.1 or -T11.2 plus anti-T11.3. It has been reported that T11.3 is a cryptic epitope which becomes accessible after activation by anti-T11.2. Most of the antibodies used so far do compete with the natural CD2 ligand LFA3 for binding (e.g., Bolhius et al., Cancer Immunol. Immunther., 34:1-8 (1991), and references cited therein).

Therefore, it was the aim of the present invention to develop new bi-specific antibodies derived from anti-tumor antibodies as well as synergistically active anti-CD2 antibodies which are capable of delivering cytotoxicity after a two-step activation while leaving the normal cross-talk of cells via CD2/LFA3 unaffected.

SUMMARY OF THE INVENTION

It has been found that the new bispecific antibodies according to the invention have the following favorable properties: strong avidity for the tumor cell, strong avidity for T-cells and NK-cells, non-competitive against LFA3, i.e., the CD2-binding site does not compete with LFA3 for the LFA3 binding site on the CD2 receptor; no synergism with LFA3, i.e., LFA3, when co-administered with the bifunctional antibodies of this invention, does not synergistically activate T- or NK-cells to cause cytotoxicity; no CD2 receptor modulation, i.e., internalization does not occur; high NK- and T-cell specificity, whereby the antibodies are effective only via a two-step activation, i.e., one BAb as such has no, or only a marginal, influence on T-cell activation and tumor cell lysis, respectively.

One object of this invention is, therefore, to provide a bispecific molecule useful for lysis of tumor cells, comprising a first binding site for an epitope of a tumor cell and a second binding site for an epitope of CD2 antigen, having the designation BAb<X, AICD2.M1>Y or BAb<X, AICD2.M2>Y, wherein BAb means bispecific antibody, X is an antibody determinant recognizing a tumor antigen, AICD2.M1, AICD2.M2 are monoclonal antibodies recognizing CD2 antigen, and Y is part of a whole antibody.

AICD2.M1 and AICD2.M2 are new monoclonal antibodies which were obtained by immunization of mice with genetically engineered CD2 antigen and isolation and purification of the antibodies from suitable mouse hybridoma cells (for details, see the Examples) and which are highly specific to CD2 antigen of T- and NK-cells.

Another object of the present invention is, therefore, a monoclonal antibody termed AICD2.M1, recognizing CD2 antigen, obtainable by isolation from the cell line 1 H 10 deposited under Accession No. DSM ACC 2118.

Yet another object of the present invention is also a monoclonal antibody termed AICD2.M2, recognizing CD2 antigen, obtainable by isolation from the cell line 7 D 3 deposited under Accession No. DSM ACC 2119.

The new cells lines producing said antibodies were deposited at "Deutsche Sammlung für Mikroorganismen" (DSM, Mascheroder WEG 1 B, D-3300 Braunsweig, Germany) according to the Budapest Treaty on Feb. 23, 1993.

The invention also relates to monoclonal antibodies which are natural or artificial variants or mutants of AICD2.M1 and AICD2.M2, whereby genetically modified or engineered, preferably humanized and chimeric versions are included.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

Lane 1: molecular weight marker,

Lane 2: MAb<AICD2.M1 >F(ab')$_2$ before reduction with DTT

Figure 3:
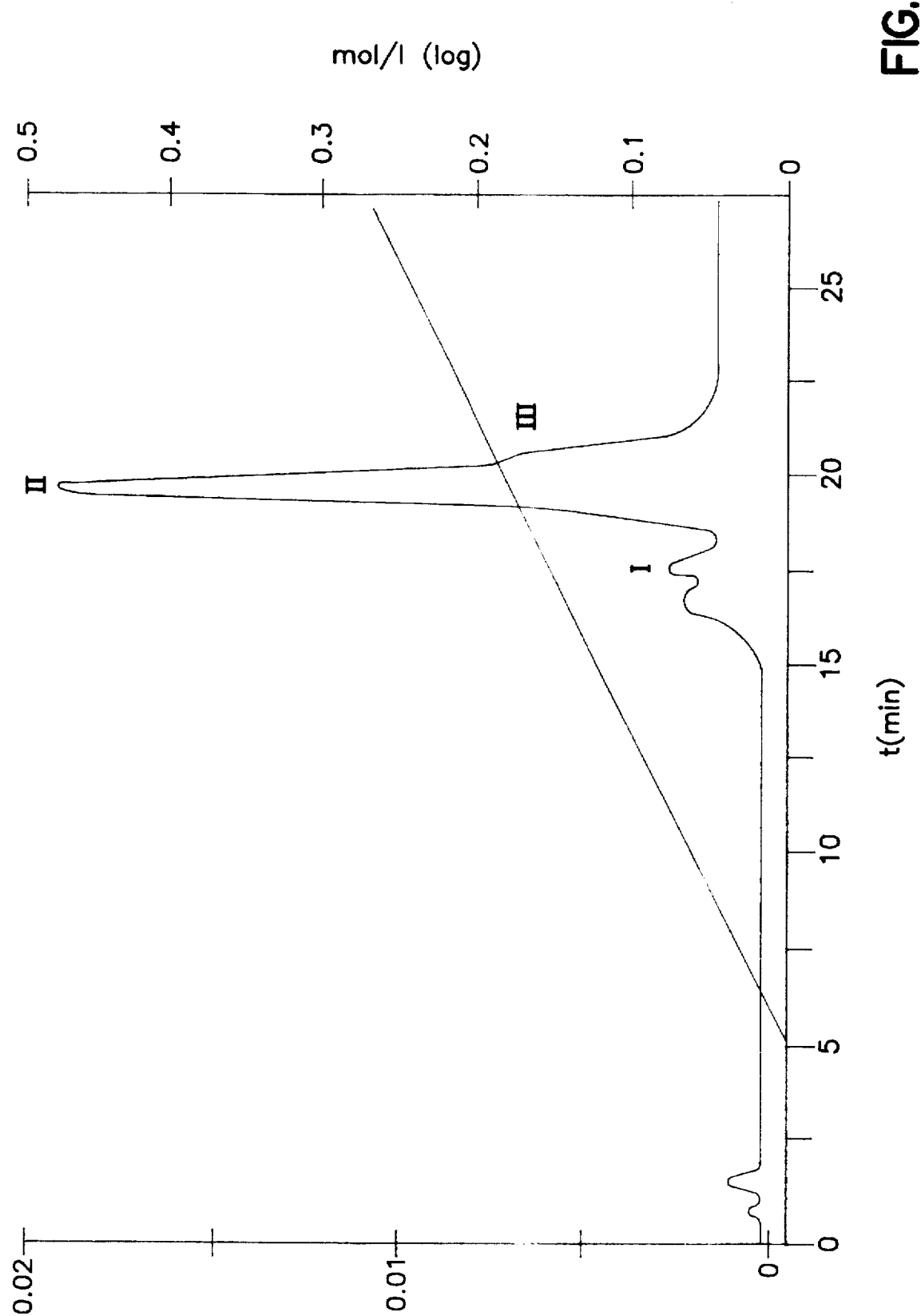
Figure 4:
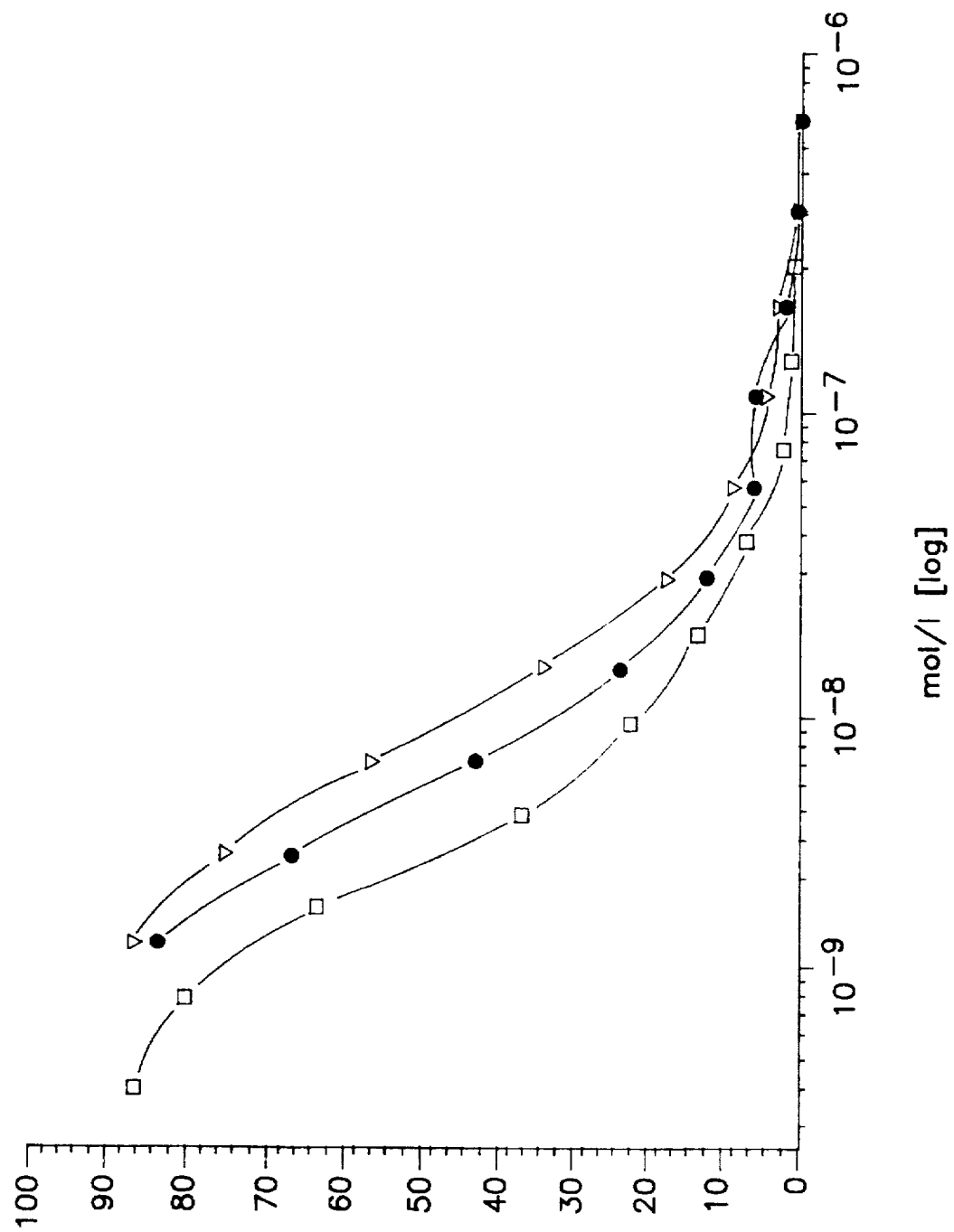

Lane 3: MAb<415>F(ab')$_2$ before reduction with DTT,

Lane 4: MAb<AICD2.M1 >F(ab')₂ after reduction with DTT and derivatization with DTNB, Lane 5: MAb<425>F(ab')₂ after reduction with DTT and derivatization with DTNB, Lane 6: BAbs before and Lane 7: BAbs after purification;

FIG. 3: Chromatographic profile of BAb<425, AICD2.M 1>F(ab')₂ on hydroxylapatite:

left vertical axis: optical density OD at 280 nm right vertical axis: concentration phosphate buffer (pH= 7.0)

horizontal axis: elution time (min), the bispecific antibody fragment is represented by peak II, peaks I and III are minor contaminates;

FIG. 4: Competitive binding of BAbs/MAbs to EGF-R:

vertical axis: % absorbance at 490 nm, horizontal axis: concentration of antibody fragments in mol/l (logarithmic scale), biotin-labeled MAb 425 has been used to compete with unlabeled MAb<425>F(ab')₂ or BAb for binding to EGF-R.

● BAb<425, AICD2.M1>F(ab')₂

▽ BAb<425, AICD2.M2>F(ab')₂

Figure 5:
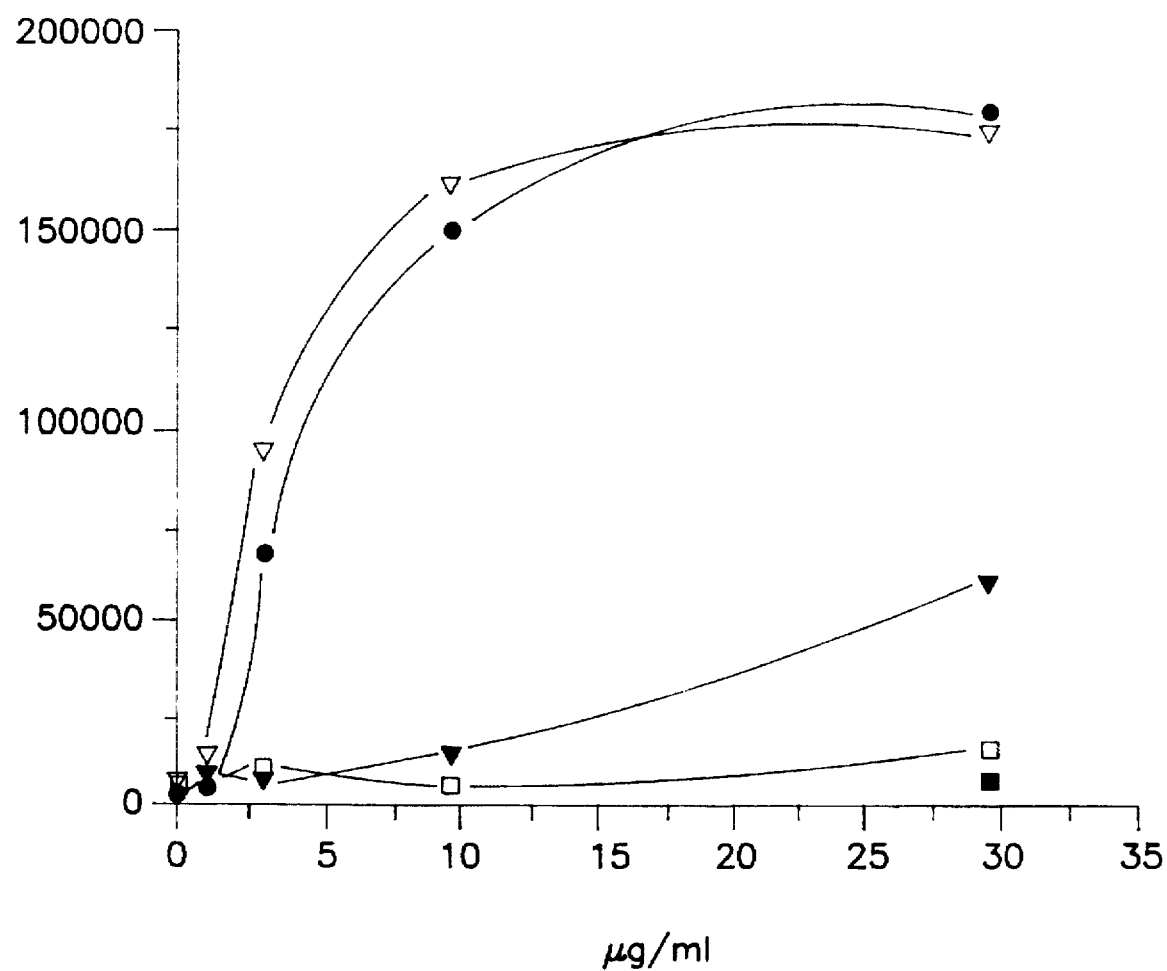

□ MAb <425>F(ab')₂;

FIG. 5: Proliferation of human peripheral blood leukocytes (PBL):

vertical axis: % incorporation of ³H-thymidine, horizontal axis: concentration of antibody fragments (µg/ml),

• BAb<425, AICD2.M1>F(ab')₂+MAb<AICD2.M2>F(ab')₂

▽ BAb<425, AICD2.M2>F(ab')₂+MAb<AICD2.M1>F(ab')₂

▼ MAb<AICD2.M2>F(ab')₂

□ MAb<AICD2.M1>F(ab')₂

Figure 6A:
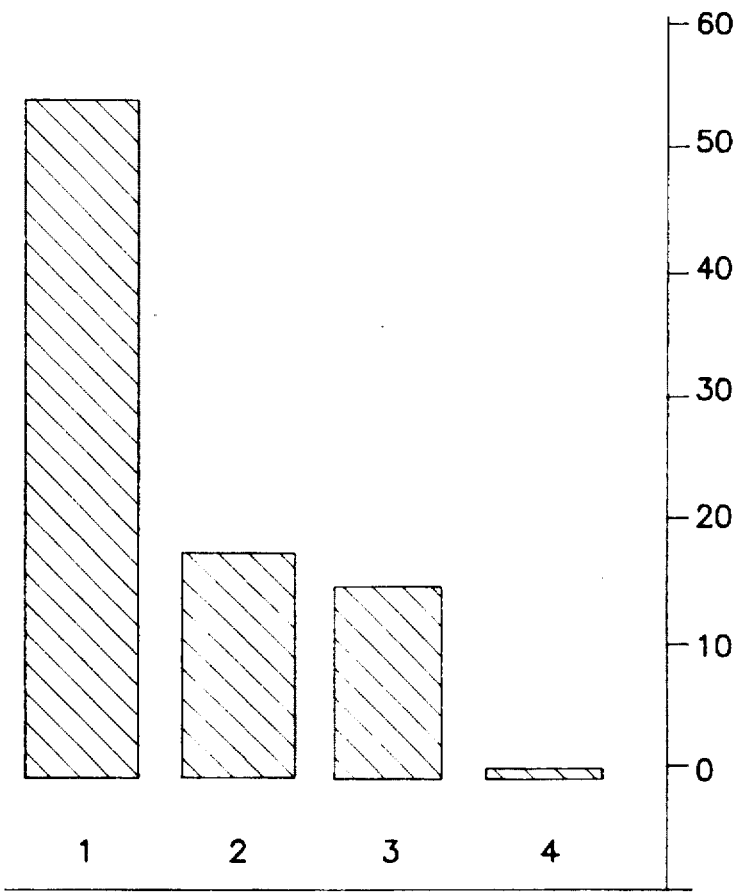
Figure 6B:
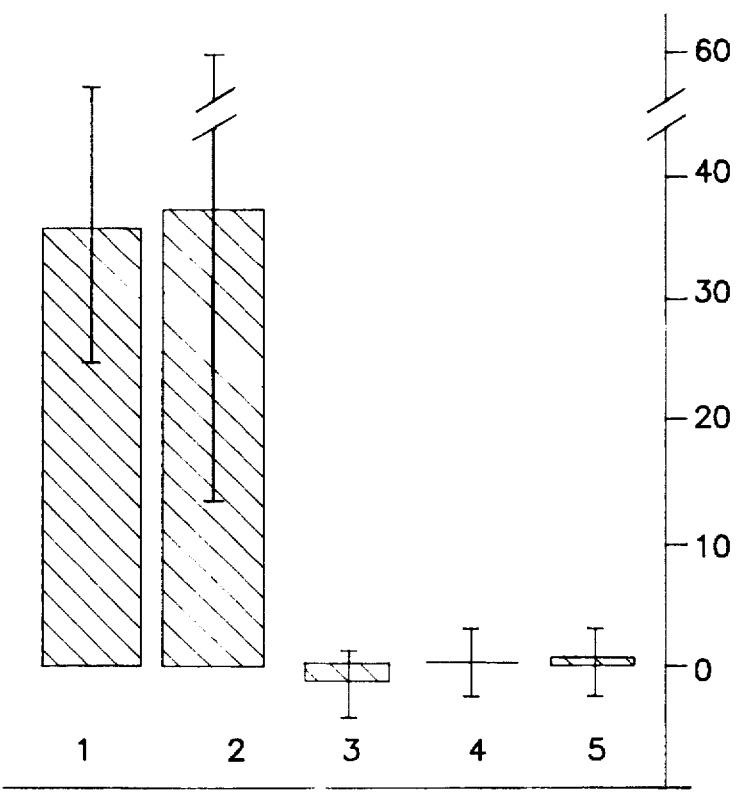
Figure 7A:
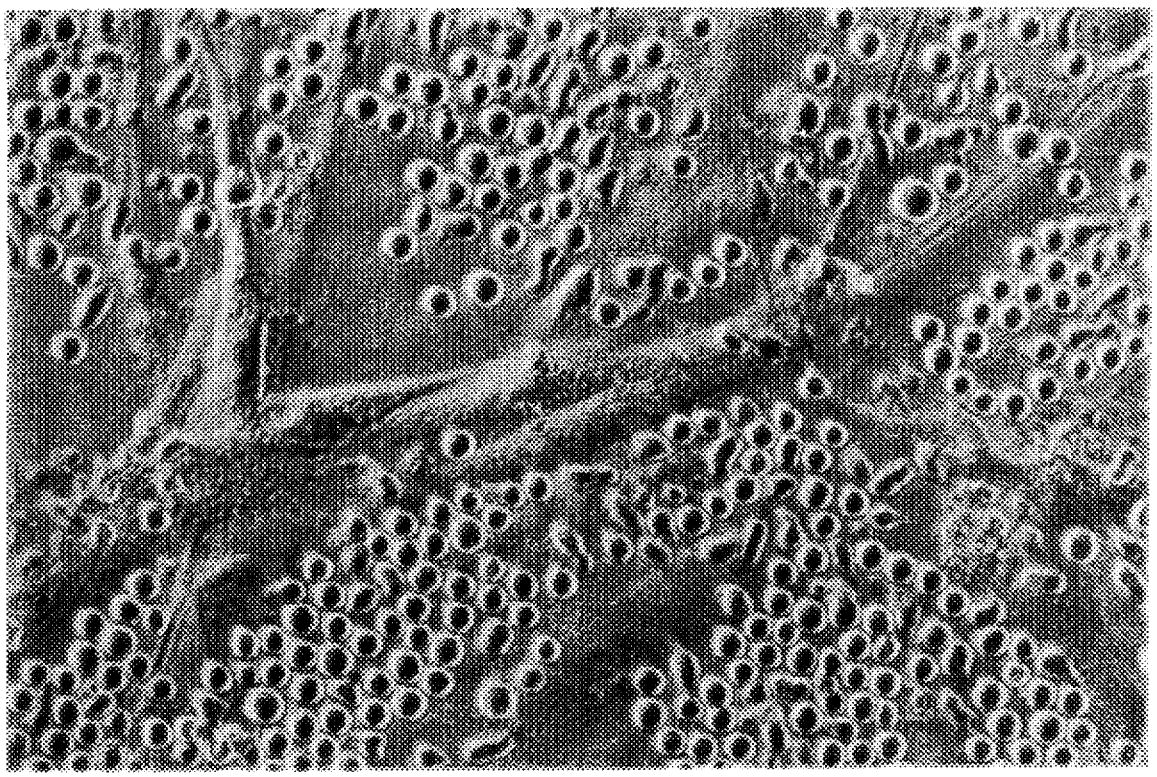
Figure 7B:
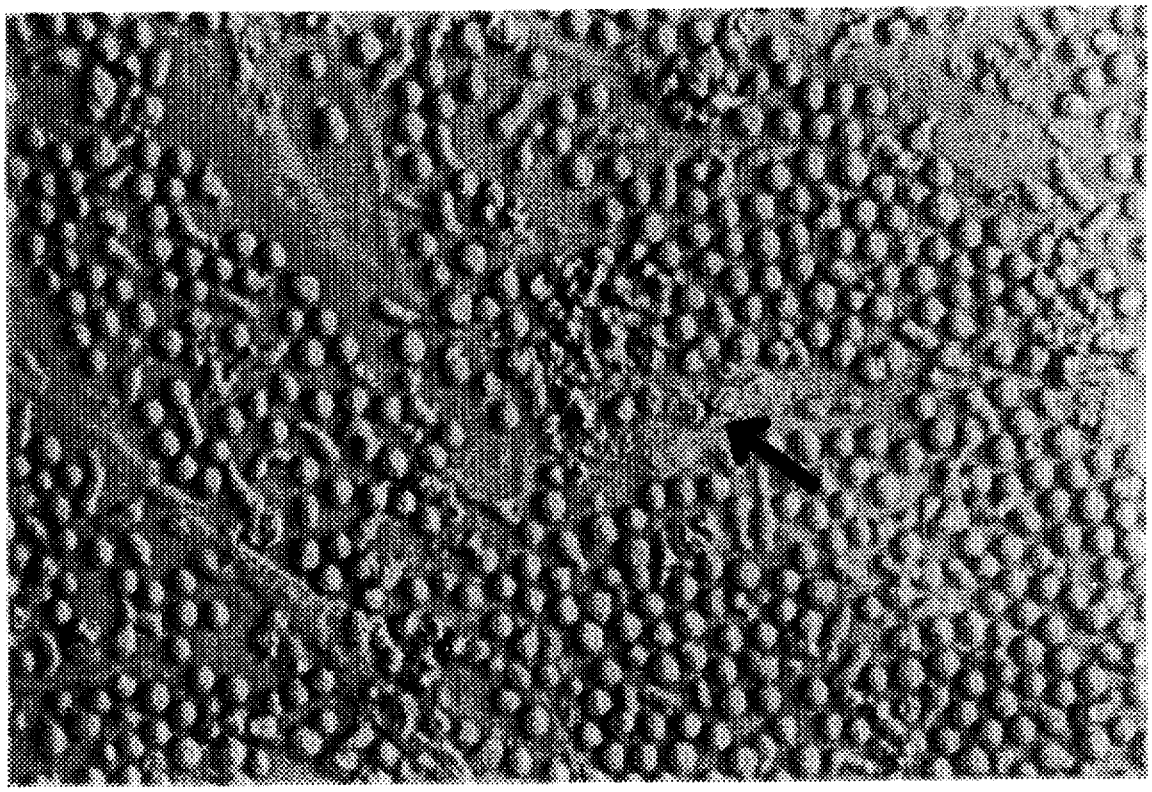

■ MAb<425>F(ab')₂;

FIG. 6A: BAb induced tumor lysis: allogeneic TILs as effector cells:

vertical axis: % cytotoxicity, horizontal axis:

1=BAb<425, AICD2.M1>F(ab')₂+ MAb<AICD2.M2>F(ab')₂
2=MAb<AICD2.M1>F(ab')₂
3=MAb<AICD2.M2>F(ab')₂
4=MAb<425>F(ab')₂;

FIG. 6B: BAb induced tumor lysis: autologous TILs as effector cell:

vertical axis: % cytotoxicity, horizontal axis:

1=BAb<425, AICD2. M 1 >F(ab')₂+ MAb<AICD2.M2>F(ab')₂
2=BAb<425, AICD2.M2>F(ab')₂+ MAb<AICD2.M1>F(ab')₂
3=MAb<AICD2.M1>F(ab')₂
4=MAb<AICD2.M2>F(ab')₂
5=MAb<425>F(ab')₂, vertical lines on top of the bars: average deviation; and FIGS. 7A and 7B: BAb mediated T-cell targeting and tumor cell lysis:

FIGS. 7A and B show a co-culture of tumor infiltrating lymphocytes (TILs) together with autologous malignant cells at an effector/target ratio of 40/1. Co-culture was incubated for 4 hours without (FIG. 7A, control) and in the presence of BAb<425, AICD2.M1>F(ab')₂+ MAb<AICD2.M2>F(ab')₂ (20 µg/ml each) (FIG. 7B). In the presence of CD2 BAb, numerous T-lymphocytes adhere and cluster to the autologous tumor cells, subsequently killing the melanoma cells. The arrow in FIG. 7B indicates a conjugate of TILs with destroyed melanoma cells. Co-culture of TILs and melanoma cells were done in 24 well plates in culture medium containing 10% FCS. Micrographs were achieved with an inverse microscope (modified phase contrast, original magnification 100).

A bispecific molecule according to the invention comprises a binding arm of AICD2.M1 or AICD2.M2 and another binding arm of an antibody which recognizes any tumor antigen. The choice of the anti-tumor antigen has no significant influence on the effectiveness of the bispecific antibody regarding T-cell activation and tumor cell lysis. In a preferred embodiment of the invention, said second binding arm is represented by a binding arm of the monoclonal anti-tumor antibody MAb 425, MAb 361 or MAb 15, whereby, according to the invention, modified, preferably humanized or chimeric versions and genetically engineered minimal fragments are included.

It is an object of the invention, therefore, to provide a bispecific antibody fragment as defined above and in the claims, wherein X is an antibody determinant derived from the monoclonal antibodies MAb 425, MAb 361 or MAb 15.

MAb 425 is a murine monoclonal antibody raised against the wellknown human A431 carcinoma cell line (ATCC CRL 1555), which binds to a polypeptide epitope of the external domain of the human EGF-R, and inhibits the binding of EGF. MAb 425 (ATCC HB 9629) was found to mediate tumor cytotoxicity in vitro and to suppress tumor cell growth of epidermoid and colorectal carcinoma-derived cell lines in vitro (Rodeck et al., Cancer Res., 47:3692 (1987)). Humanized and chimeric versions of MAb 425 have been disclosed in WO 92/15683.

MAb 361 is an IgG2a murine monoclonal antibody (ATCC HB 9325) which binds specifically to the ganglioside GD2 antigen and GD3 antigen. These gangliosides are greatly enriched in melanoma tumors (EP 0 280 209, U.S. Ser. No.016,902). MAb 361 shows a significant level of cytotoxicity in vitro against tumor cells expressing GD2 antigen (Thurin et al., Cancer Res., 47:1229 (1987)).

MAb 15 is an IgG 1 murine monoclonal antibody generated by immunization with the human small cell lung cancer cell TKB-2 (Endo et al., Cancer Res., 46:6369 (1986)). The antibody recognizes an early differentiation antigen.

The bispecific antibodies according to the invention are fragments of whole antibodies, for example, F(ab')₂ molecules or miniantibodies (Fv molecules), preferably F(ab')₂ molecules. In contrast to whole antibodies, fragments such as F(ab')₂ and miniantibodies may penetrate into the tumor mass of solid tumors more easily and reveal their cytotoxicity and power of cell lysis within the tumor. Moreover, F(ab')₂ molecules and miniantibodies derived from murine sources normally show a reduced human anti-mouse antibody response (HAMA).

Therefore, it is a preferred object of this invention to provide a bispecific antibody fragment as defined above wherein Y is a F(ab')₂ molecule. Especially preferred embodiments are selected from the group:

BAb<424, AICD2.M1>F(ab')₂,
BAb<425, AICD2.M2>F(ab')₂,
BAb<361, AICD2.M1>F(ab')₂,
BAb<361, AICD2.M2>F(ab')₂,
BAb<15, AICD2.M1>F(ab')₂,

BAb<15, AICD2.M2>F(ab')$_2$.

Various methods to produce bispecific antibodies based on complete antibodies or fragments have been described (e.g., see review article of Brissinck et al., Drugs of the Future, 17(11): 1003 (1992)). One way to construct bispecific antibody fragments is to convert whole antibodies into (monospecific) F(ab')$_2$ molecules by proteolysis, splitting these fragments into the Fab' molecules and recombine Fab' molecules with different specificity to bispecific F(ab')$_2$ molecules (see, for example, EP 0 179 872 B1).

Thus, it is an object of the present invention to provide a method of preparing a bispecific antibody F(ab')$_2$ fragment useful for lysis of tumor cells comprising a first binding site specific for an epitope of a tumor cell and a second binding site specific for an epitope of CD2 antigen by enzymatic conversion of two different monoclonal antibodies, each comprising two identical L (light chain)-H (heavy chain) half molecules and linked by one or more disulfide bonds, into two F(ab')$_2$ molecules, splitting each F(ab')$_2$ molecule under reducing conditions into the Fab' thiols, derivatizing one of these Fab' molecules of each antibody with a thiol activating agent and combining an activated Fab' molecule bearing tumor specificity with a non-activated Fab' molecule bearing leukocyte specificity or vice versa in order to obtain the desired bispecific antibody F(ab')$_2$ fragment, characterized in that monoclonal antibodies AICD2.M1 and AICD2.M2 are used as antibody recognizing leukocyte antigen.

As enzymes suitable for the conversion of an antibody into its F(ab')$_2$ molecules, pepsin and papain may be used. In some cases, trypsin or bromelin are suitable. Pepsin, however, is preferably used in the process of the present invention. The conversion of the disulfide bonds into the free SH-groups (Fab' molecules) may be performed by reducing compounds, such as dithiothreitol (DTT), mercaptoethanol, and mercaptoethylamine. Thiol activating agents according to the invention which prevent the recombination of the thiol half-molecules, are 5,5'-dithiobis(2-nitrobenzoic acid) (DTNB), 2,2'-dipyridinedisulfide, 4,4'-dipyridinedisulfide or tetrathionate/sodium sulfite (see also Raso et al., Cancer Res., 42:457 (1982), and references incorporated therein). Preferably, DTNB is used in the process according to this invention.

The treatment with the thiol-activating agent is generally performed only with one of the two Fab' fragments. Principally, it makes no difference which one of the two Fab' molecules is converted into the activated Fab' fragment (e.g., Fab'-TNB). Generally, however, the Fab' fragment being more labile is modified with the thiol-activating agent. In the present case, the fragments bearing the anti-tumor specificity are slightly more labile, and, therefore, preferably used in the process. The conjugation of the activated Fab' derivative with the free hinge-SH groups of the second Fab' molecule to generate the bivalent F(ab')$_2$ antibody occurs spontaneously at temperatures between 0° and 30° C. The yield of purified F(ab')$_2$ antibody is 20-40% (starting from the whole antibodies).

As mentioned above, the invention includes also bispecific miniantibodies. Miniantibodies are antibody fragments comprising two single-chain Fv fragments (scFv fragments are usually genetically linked either as $V_H$-linker-$V_L$ or as $V_L$-linker-$V_H$) which are linked by, e.g., autoaggregation or by fusing each of them at the C-terminus to a hinge region (optionally) to provide flexibility, and/or an amphipathic helix to achieve dimerization. The helix can be taken from a four-helix-bundle design or from a leucine zipper (e.g., Pack and Pluckthun, Biochem., 31:1579 (1992)).

Alternatively, the heterologous Fv regions can be crosslinked by conventional known crosslinking means, e.g., using heterobifunctional crosslinkers such as those disclosed in Segal and Snider, Chem. Immunol., 47:179 (1989); Glennie et al., J. Immunol., 139:2367 (1987); Brennan et al., Science, 229:81 (1985); and PCT/US91/07283 (Romet-Lemonne and Fanger, references incorporated therein included). The preparation of miniantibodies as defined above, is disclosed, for example, in WO 93/00082.

The bispecific antibody fragments according to the invention were tested in vitro/ex vivo regarding the following properties: the capacity to bind to the specific tumor- and T-cells, immunomodulation (T-cell proliferation) and cytotoxicity (tumor cell lysis). The tests are described per se in the standard literature. Details and results are given in the Examples.

The bispecific antibody fragments according to the invention can be administered to human patients for therapy. Therefore, it is an object of the invention to provide a pharmaceutical formulation comprising as active ingredient at least one bispecific antibody fragment as defined above and in the claims, associated with one or more pharmaceutically acceptable carrier, excipient or diluent therefor.

Typically, the antibody fragments of this invention will be injected intravenously or parenterally. Generally, the dosage ranges for the administration of the bispecific antibody fragments are large enough to produce the desired tumor-suppressing and tumor-lysing effects. The dosage will depend on age, condition, sex and extent of the disease in the patient and can vary from 0.1 mg/kg to 200 mg/kg, preferably from 0.1 mg/kg or 100 mg/kg/dose in one or more dose administrations daily, for one to several days.

Preparations for parenteral administration include sterile aqueous or non-aqueous solutions, suspensions, and emulsions. Examples of non-aqueous solvents are propylene glycol, polyethylene glycol, vegetable oils such as olive oils, and injectable organic esters such as ethyl oleate and other solvents known in the art which are suitable for these purposes. The bispecific antibodies of this invention can be used in a composition comprising a physiologically acceptable carrier. Examples of such suitable carriers are saline, PBS, Ringer's solution, or lactated Ringer's solution. Preservatives and other additives such as antibiotics, antioxidants, and chelating agents may also be present in the pharmaceutical formulations. The bispecific antibody fragments can also be conjugated according to known methods, e.g., as disclosed above, to cytokines such as IL-2 in order to support their cytotoxicity. See, e.g., Remington's Pharmaceutical Sciences, 18th ed., A. R. Gennaro, ed., Mack Publishing, Easton, Pa. (1990).

The pharmaceutical formulations of the present invention are suitable for the treatment of all kinds of tumors, including melanomas, gliomas and carcinomas, as well as tumors of the circulating system and solid tumors. Preferred formulations comprise a bispecific antibody fragment, wherein one binding arm bears the binding sites of the monoclonal antibodies MAb 425, MAb 361 or MAb 15.

The present invention discloses a very effective two-step activation of leukocytes by administration by two different antibodies or specific antibody fragments, respectively. By a two-step activation is meant that, unless (a) a first formulation comprising a bispecific antibody fragment having a defined tumor cell specificity and a CD2 binding site, is administered with (b) a second formulation comprising an additional different bispecific antibody fragment having a different CD2 binding site but the same tumor cell specificity, or a monoclonal antibody having a different CD2 binding site but no tumor specificity, or a fragment of said antibody, the first bispecific antibody fragment is either ineffective or only marginally (20–40%) effective as a single agent.

Therefore, it is an object of the invention to provide a pharmaceutical kit of parts (A) comprising a first pharmaceutical formulation (I) as defined above or in the claims comprising a bispecific antibody fragment BAb<X, AICD2.M2>Y, and a second separate pharmaceutical formulation (II) comprising MAb AICD2.M1 or MAb<AICD2.M1>Y or BAb<X, AICD2.M1>Y, wherein X and Y have the indicated meanings. In this pharmaceutical kit of parts, formulation (I) is founded on MAb AICD2.M2 and formulation (II) on MAb AICD2.M1.

Alternatively, the invention relates to a kit of parts (B) wherein formulation (I) is based upon MAb AICD2.M1, whereas formulation (II) is founded on MAb AICD2.M2. Thus, it is a further object of this invention to provide a pharmaceutical kit of parts comprising a first pharmaceutical formulation (I) comprising a bispecific antibody fragment BAb<X, AICD2.M1>Y, and a second separate pharmaceutical formulation (II) comprising MAb AICD2.M2 or MAb<AICD2.M2>Y or BAb<X, AICD2.M2>Y, wherein X and Y have the indicated meanings.

The differences between compositions (A) and (B) are normally not very significant. In the case of MAb 425, it can be seen that the composition (B), wherein formulation (I) is based on MAb AICD2.M1, works better.

Differences in tumor binding sites within a composition ((A) or (B)) are also generally not very significant. The effectiveness of the pharmaceutical kits of parts according to the invention regarding binding capacity, immunomodulation (leukocyte proliferation) and cytotoxicity depends, however, on the influence of the binding sites of the bispecific antibody fragments which derive from the antibodies AICD2.M1 and AICD2.M2. Thus, the preferred embodiments of this invention show similar properties.

Differences in therapeutical effect regarding formulation (II) (alternatively whole antibody, monospecific antibody fragment or BAb) are also not very dramatic. However, formulation (II), comprising the suitable monospecific antibody fragment, is preferred.

The pharmaceutical kit of parts is used as follows. Medical treatment is started by injecting formulation (I) of one of the pharmaceutical kit of parts according to the invention into the patient. The bispecific antibody binds according to its specificity not only to the surface of the tumor, but for reasons of its small size, it may also penetrate into the solid tumor mass. The administration of the bispecific antibody fragment according to the invention causes an enrichment of injected immunoglobulin in the local area of the tumor, but does not yet lead to a significant immune response. After a given time period (which can be routinely determined and which is dependent on extent of disease, type of tumor, condition, sex and age of the patient) of several hours to several days, formulation (II) is administered and immunological responses are induced immediately. Formulations (I) and (II) are preferably administered in equimolar amounts. Ex vivo experiments show that autologous and allogeneic tumor-infiltrating lymphocytes (TILs) which are normally unable to induce significant cytotoxicity against the tumor (cell lysis) can be highly activated by said treatment (FIGS. 6a, 6b and 7).

By means of a pharmaceutical kit of parts according to this invention, it is also possible to purge ex vivo tumor cells in bone marrow preparations. In order to intensify the cytotoxic effect, it is possible to add exogenous T-lymphocytes.

Therefore, it is also an object of the present invention to provide a method for purging of tumor cells ex vivo in autologous bone marrow transplantation by means of a pharmaceutical kit of parts as defined above or in the claims, optionally in the presence of additional T-lymphocytes, whereby, to begin with, the cells are treated with formulation (I) and, after that, with formulation (II), optionally followed by a conventional purification step. The techniques of purging bone marrow ex vivo are well known in the art per se.

The bispecific antibody fragments of the present invention can also be used to identify and/or purify molecules containing the epitopes for which the binding sites are specific, using methods and under conditions well known to one of ordinary skill in the art. Thus, for example, the bispecific antibody fragments can be bound to a column matrix for purification of tumor antigen or CD2 antigen. Additionally, the bispecific antibody fragments can be used in conventional immunoassay procedures to identify and quantitate tumor antigen or CD2 antigen, e.g., for diagnostic purposes.

Screening of, for example, EGF-R-positive tumors may be performed with biopsy or histological materials according to known methods (e.g., Soler et al., Am. J. Pathol., 118(3):439 (1985); Brandon, J. Histochem. Cytochem., 33:715 (1985); Kachidian et al., J. Neurosci. Res., 30(3):21 (1991). EGF-R positive tumors are suitable for bispecific antibody treatment as described above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding European application EP 93112330. 1, filed Aug. 2, 1993, are hereby incorporated by reference.

Monoclonal cell lines producing MAb 425 (ATCC CRL 1555) and MAb 361 (ATCC HB 9325) were deposited with the (ATCC, 12301 Parklawn Dr., Rockville, Md., USA, in accordance with the Budapest Treaty, and are now publicly available.

EXAMPLES

Example 1: Preparation of MAbs AICD2.M1 and AICD2.M2

Balb/C mice were immunized four times within two weeks with genetically engineered CD2. The DNA sequence of human CD2 and its cloning has been described by Sayre et al., Proc. Nat'l Acad. Sci. (USA), 84:2941 (1987). The CD2 gene expression was done in the Baculovirus system according to methods known in the literature (e.g., Fraser, Current Topics in Microbiol. Immunol., 158:131 (1992), and references cited therein).

Spleen cells of immunized mice were isolated and fused with the myeloma cell line (Ag8.653, ATCC CRL 1580). Hybridomas were screened for specific monoclonal antibody production by testing the supernatants of growing hybridomas on human T-lymphocytes (CD2 positive) by means of fluorescence-activated cell sorter (FACS). Positive hybridomas were recovered by the method of "limited dilution cloning." The supernatants of the selected hybridomas were investigated by means of immunoprecipitation and western blot analysis. The isolation of the selected monoclonal antibodies was achieved by purification of cultures of supernatants according to Ey et al., Immunochemistry, 15:429 (1978).

Functional analysis of the antibodies directed to the CD2 antigen was done by means of a proliferation test (incorporation of $^3$H-thymidine). Two antibodies selected from a series of monoclonal antibodies reacting with CD2 antigen strongly induced the proliferation of T-cells. These monoclonal antibodies were designated as AICD2.M1 and AICD2.M2 and deposited at Deutsche Sammlung für Mikroorganismen.

All used methods were achieved by standard procedures. Many of them are disclosed, for example, in "Antibodies, a Laboratory Manual," Harlow and Lane, Cold Spring Harbor (1988), and references cited therein.

Example 2: Synthesis of BAb<425, AICD2.M1 >F(ab')$_2$

Figure 1:
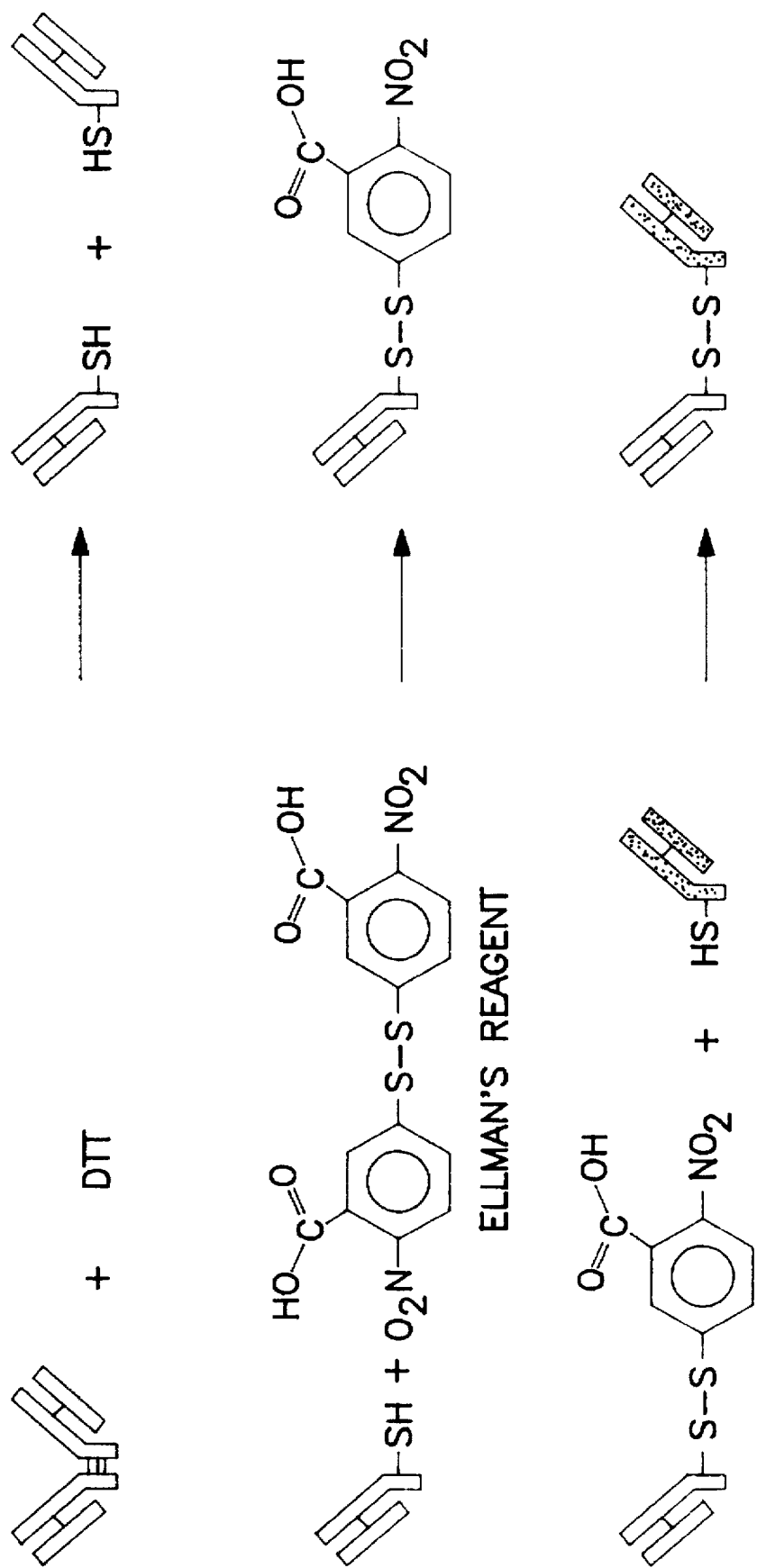
FIG. 1: Synthesis of BAbs (scheme)

Synthesis started from 10 mg of the antibody AICD2.M1 and 10 mg of the antibody MAb 425. Antibodies used were treated by pre-activated papain-treatment (10 mg/ml) in citric acid buffer, 3 mM EDTA, pH 5.5. After proteolysis, F(ab')$_2$ was recovered from the eluate of a protein A-sepharose column. The recovery of F(ab')$_2$ is generally close to 100%. Both F(ab')$_2$ fragments were individually converted into the Fab' fragment by treatment with 0.5 mM DTT for 40 min. at 30° C. After the reduction step, surplus DTT was removed and Fab' recovered via gel filtration (Superdex® 200). In the ongoing process, the Fab'-TNB derivative was generated by treating the MAb 425 fragment with 0.5 mM Ellman's reagent (5,5'-dithio-bis-(2-nitrobenzoic acid) (DTNB)) at 4° C. for 60 min. Surplus DTNB was removed by gel filtration. 6 mg of each conjugation partner (Fab' - AICD2.M1 and Fab'-TNB MAb 425) was used for the final conjugation step by stirring the mixture of the conjugation partners at 4° C. for 18 hours. Bispecific antibody was recovered from the reaction mixture by gel filtration chromatography (Superdex® 200). The yield of the synthetic F(ab')$_2$ preparation was in a range of 3–4 mg (≈30%). The sequences of operations involved in BAb synthesis are summarized in FIG. 1.

Example 3: Synthesis of BAb<361, AICD2.M1 >F(ab')$_2$

According to Example 2, a bispecific antibody was prepared starting from MAb AICD2.M1 and MAb 361. The yield of BAb was approximately 34%.

Example 4: Synthesis of BAb<15, AICD2.M1 >F(ab')$_2$

According to Example 2, a bispecific antibody was prepared starting from MAb AICD2.M1 and MAb 15. The yield of BAb was approximately 23%.

Example 5: Synthesis of BAb<425, AICD2.M2 >F(ab')$_2$

According to Example 2, a bispecific antibody was prepared starting from MAb AICD2.M2 and MAb 425. The yield of BAb was approximately 30%.

Example 6: Synthesis of BAb<425, AICD2.M1>(scFv)$_2$

Two single chain proteins consisting of the $V_L$ and $V_H$ domains of AICD2.M1 and MAb 425 have been prepared by molecular engineering (Winter et al., Nature, 349:293–299 (1991)). The expression plasmids were derived from pHEN 1 (Hoogenboom et al., Nucleic Acid Res., 19:4133–4137), which contains the structural genes for the $V_L$ and $V_H$ domains derived from either the anti-EGF-R murine hybridoma (MAb 425) or the anti-CD2 murine hybridoma (AICD2.M1). The pelB leader sequence was used to mediate periplasmic secretion in E. coli. scFv's were purified by affinity chromatography and used for the construction of bispecific scFv. Chemical crosslinking of EGF-r and CD2-specific scFv's was done with the help of the reagent 2-iminothiolane (2-imino-tetrahydrothiophene) and the heterobifunctional crosslinker SPDP (succinimidyl-3-(2-pyridyl-dithiol)-propionate). Starting from 10 mg of MAb <425>scFv, we have approached the statistical incorporation of one molecule of 2-pyridyl-disulfide per scFv molecule via SPDP. Purification of the derivative was performed with gel filtration chromatography. Introduction of a reactive-SH group into the MAb<AICD2.M1>scFv was obtained by derivatization of 10 mg scFv with 2-iminothiolane. Purification of the derivative was performed with gel filtration chromatography. Equimolar quantities of 2-pyridyl-disulfide activated MAb<425>scFv and the 2-iminothiolane modified MAb<AICD2.M 1>scFv were coupled together at neutral pH. The coupling reaction was followed by monitoring the liberation of pyridine-2-thione. The final bispecific product was recovered by gel filtration chromatography with a yield of about 5%.

Example 7: Characterization of the bispecific antibodies

Figure 2:
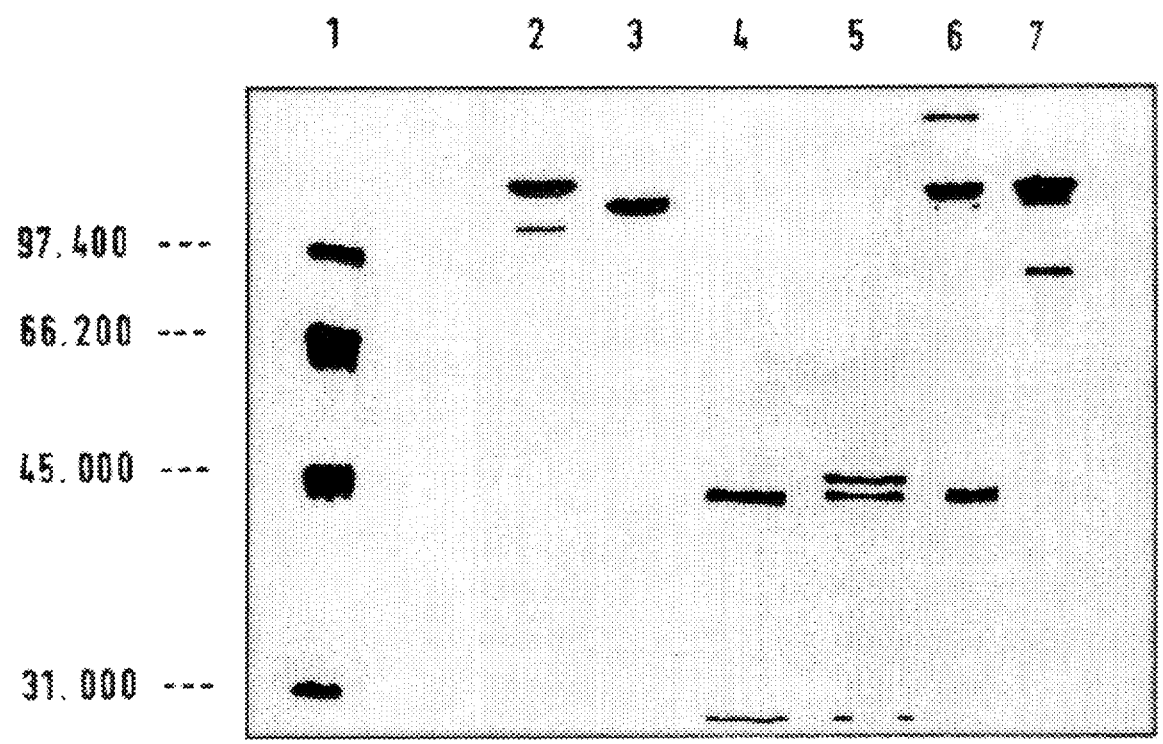
FIG. 2: SDS-PAGE of antibody fragments and BAbs.

The individual steps of BAb synthesis was monitored by SDS-PAGE according to usual known techniques. The intermediates of the chemical synthesis and the final bispecific products are shown in FIG. 2. In addition to SDS-PAGE analysis, purity and homogeneity of BAb was assessed by chromatography on a hydroxylapatite column. Elution of BAb was performed with a gradient of phosphate buffer (pH =7.0, 0–0.3 mol/l). FIG. 3 shows the chromatographic profile of BAb<425, AICD2.M1>F(ab')$_2$. The BAb is represented by the major peak 11; the smaller peaks I and III are minor contaminants.

Example 8: Binding properties of BAb<425, AICD2.M1>F(ab')$_2$ to EGF-R

The binding properties of the bispecific antibody was compared by competitive ELISA assay. In summary, biotin-labeled MAb 425 was used to compete with unlabeled antibody or BAb's for binding to EGF-R. EGF-R was isolated from A 431 cells (ATCC CRL 1555) according to known methods.

A 431 cells are CD2 negative. Detection was done after incubation with peroxidase-conjugated streptavidin and substrate (Harlow and Lane, "Antibodies, A Laboratory Manual," Cold Spring Harbor (1988)). From the data, inhibition curves were constructed (FIG. 4). The inhibition curves for both BAb's were shifted to the right, indicating loss in affinity due to change from divalent to monovalent binding.

Example 9: Binding properties of BAb<MAb 425, AICD2.M2 >F(ab')$_2$ to EGF-R

According to Example 8, the binding properties of the bispecific antibody were investigated (FIG. 4). Both BAbs were of comparable avidity toward their antigen target.

Example 10: Binding properties of bispecific and monospecific antibody fragments to CD2 antigen Jurkat cells (human acute T-cell leukemia, CD2, CD3 positive, EGF-R negative; ATCC TIB 152) were incubated (1×10$^6$ cells/sample) with logarithmical dilutions of the bispecific/monospecific antibody fragment for 15 minutes at about 4° C. Cells were then washed and incubated with goat-anti-mouse-kappa-FITC as a second step antiserum. Cells were washed again and immunofluorescence was analyzed with a FACStar plus®. The FACStar plus® with single laser excitation and list mode data acquisition was used to analyze antibody staining of living cells. The specific fluorescence intensities of the whole cell population and the percentage of antibody reactive cells were determined. Fluorescence distributions of cells stained only with the second step antiserum served as negative controls.

In the following table, half-saturating concentrations ($conc._{1/2}$ sat.) as a measure of binding strength of the different bispecific/monospecific antibody fragments on Jurkat cells are indicated. Values for $conc._{1/2}$ sat.were read from the titration curves (fluorescence intensity (linear presentation) versus antibody concentration) and thus are rough estimations.

| Antibody Fragment | $Conc._{1/2\ sat.}$ |
| --- | --- |
| MAb < AICD2.M1 > F(ab')$_2$ | $3 \times 10^8$ |
| BAb < 425, AICD2.M1 > F(ab')$_2$ | $>1 \times 10^7$ (no satur.) |
| BAb < 361, AICD2.M1 > F(ab')$_2$ | $1 \times 10^7$ (no satur.) |
| MAb < AICD2.M2 > F(ab')$_2$ | $2 \times 10^8$ |
| BAb < 525, AICD2.M2 > F(ab')$_2$ | $>1 \times 10^7$ (no satur.) |
| BAb < 15, AICD2.M2 > F(ab')$_2$ | $1 \times 10^7$ (no satur.) |
| BAb < 425 > F(ab')$_2$ | negative |

Example 11: Proliferation of leukocytes

Peripheral blood mononuclear leukocytes were co-cultured with irradiated (30 Gy) autologous tumor cells in medium (RPMI 1640) supplemented with IL-2 (20 U/ml) and IL-4 (1000 U/ml). Responder cells were weekly restimulated with autologous tumor cells.

Freshly prepared human peripheral blood leukocytes (huPBL) from healthy blood donors or melanoma patients were cultured in 96 well flat-bottom microtiter plates in a final volume of 200 μl at a density of $1 \times 10^5$ cells/well. Cells were incubated with monospecific or monospecific+ bispecific antibody fragments in indicated concentrations. After 72 hours, the cells were pulsed with 0.5 μCi $^3$H-thymidine, incubated overnight, and harvested. The incorporation of $^3$H-thymidine was measured by liquid scintillation β-plate counting, and the results expressed as the average cpm. The results for antibody fragments derived from MAb 425 can be seen in detail from FIG. 5. Similar results were obtained using antibody fragments derived from MAb 361 and MAb 15. Combined administration of antibody fragments causes a significant induction of proliferation in each of these cases.

Example 12: BAb induced tumor lysis

The cell line C8161, a highly invasive and spontaneously metastatic, EGF-R positive human melanoma cells line (Welch et al., Int. J. Cancer, 47:227 (1991), and references cited therein) was used as target for EGF-R 30 dependent targeting by the allogeneic and autologous tumor infiltrating T-lymphocytes (TILs). Other EGF-R positive human melanoma cell lines can also be used. TIL bulk culture was established from a melanoma specimen. Culture conditions of tumor cells and TILs have been described previously (e.g., Shimizu et al., Cancer Res., 51:6153 (1991)).

Production of stable CTL clones has been done with MLTC (Mixed Lymphocyte T-cells) responder cells under limiting dilution conditions. MLTC responder T-cells were seeded at one cell per well in 96-well plates in medium supplemented with IL-2 and IL-4 together with autologous stimulatory cells and autologous EBV-transformed B cells as feeder cells. Colonies were weekly re-stimulated with autologous tumor cells and feeder cells.

T-lymphocytes from fresh tumor biopsies were activated with immobilized anti-CD3 antibody and expanded in RPMI supplemented with IL-2 and IL-4.

In vitro cytotoxicity assays were performed using $^{51}$Cr-labeled tumor cells. Target cells were labeled with $^{51}$Cr (100 mCi/$10^7$ cells) for 1 hr. and washed 3 times. A constant number of labeled cells ($2 \times 10^3$/well) were co-incubated with monospecific or bispecific antibody or a combination of them together with effector TILs in an effector/target ratio of 7/1. CTL were serially diluted in triplicates in 100 ml of medium in 96-well microtiter plates. After adding labeled target cells, the plates were incubated 4 hrs. at 37° C. in 10% $CO_2$. The assays were stopped by centrifugation. The supernatants were collected and radioactivity was measured with a gamma-counter. Percent specific $^{51}$Cr-release was calculated according to the formula:

$$\% \text{ specific}^{51}\text{Cr-release} = 100 \frac{(\text{experimental release-spontaneous release})}{(\text{maximum release-spontaneous release})}$$

The results for antibody fragments derived from MAb 425 can be seen in detail from FIGS. 6A, 6B, 7A and 7B. Similar results were obtained using antibody fragments derived from MAb 361 and MAb 15. Combined administration of antibody fragments causes a significant induction of tumor lysis in each of these cases.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A molecule which is a bispecific antibody fragment, comprising
   (a) a first binding site specific for an epitope on a tumor cell antigen and
   (b) a second binding site specific for an epitope of antigen CD2, selected from the group consisting of AIDC2.M1 and AICD2.M2,
   of the formulae BAb<X,AICD2.M1>Y or BAb<X, AICD2.M2>Y, wherein
   BAb≦indicates the molecule is a bispecific antibody,
   X is a first antibody determinant specific for an epitope on a tumor cell antigen,
   AICD2.M1 and AICD2.M2 are antibody determinants of antibodies AICD2.M1 and AICD2.M2, respectively, which are specific for antigen CD2, and
   ≧Y indicates the molecule is an antibody fragment.

2. A bispecific antibody fragment of claim 1, wherein X is an antibody determinant derived from monoclonal antibodies MAb 425 (ATCC HB 9629) or MAb 361 (ATCC HB 9325).

3. A bispecific antibody fragment of claim 1, wherein Y indicates the molecule is an F(ab')$_2$ molecule.

4. A bispecific antibody fragment of claim 3, selected from
   BAb<425,AICD2.M1>F(ab')$_2$,
   BAb<425,AICD2.M2>F(ab')$_2$,
   Bab<361,AICD2.M1>F(ab')$_2$, or
   BAb<361,AICD2.M2>F(ab')$_2$.

5. A bispecific antibody fragment of claim 1, wherein Y indicates the molecule is an Fv molecule.

6. A bispecific antibody fragment of claim 1, wherein said bispecific antibody fragment is cytotoxic for a tumor cell carrying said tumor cell epitope.

7. A bispecific antibody fragment of claim 1, wherein said bispecific antibody fragment is capable of triggering T-cell or NK-cell mediated cell lysis of a tumor cell carrying said tumor cell epitope.

8. A bispecific antibody fragment of claim 1, wherein said bispecific antibody fragment does not compete with LFA3 (CD58) for binding to CD2.

9. A bispecific antibody fragment of claim 1, wherein said bispecific antibody fragment demonstrates strong avidity for said tumor cell, strong avidity for T-cells and NK-cells, no receptor modulation, and/or high NK- and T-cell specificity, whereby said bispecific antibody fragment alone is ineffective or marginally effective to activate T-cell or NK-cell mediated cell lysis of a tumor cell carrying said tumor cell epitope, but is therapeutically effective to activate T-cell or NK-cell mediated cell lysis of a tumor cell carrying said tumor cell epitope only via a two-step activation with a second, different antibody, antibody fragment, bispecific antibody or bispecific antibody fragment having a binding site specific for an epitope of antigen CD2.

10. A method for preparing a bispecific antibody fragment of claim 1, comprising enzymatically converting each of two different monoclonal antibodies (a') and (b'), wherein
- (a') has a first binding site specific for an epitope on a tumor cell antigen, and
- (b') has a second binding site specific for an epitope of leukocyte antigen CD2, and
- wherein each antibody comprises two identical light chain and heavy chain half molecules linked by one or more disulfide bonds, into two F(ab')$_2$ molecules,
- splitting each F(ab')$_2$ molecule under reducing conditions into Fab' thiols,
- derivatizing the Fab' molecules derived from either antibody (a') or (b') with a thiol activating agent, and
- combining the thus-derivatized Fab' molecule with the corresponding other Fab' molecule derived from antibody (b') or (a') to produce a bispecific antibody F(ab')$_2$ fragment bearing both tumor specificity and leukocyte specificity,
- wherein said monoclonal antibody (b') specific for an epitope of leukocyte antigen CD2 is selected from the group consisting of AICD2.M1 and AICD2.M2.

11. A method of claim 10, wherein the monoclonal antibody (a') is MAb 425 (ATCC HB 9629), MAb 361 (ATCC HB 9325).

12. Monoclonal antibody AICD2.M1, which is specific for an epitope of antigen CD2, and is obtainable by isolation from hybridoma cell line 1 H 10 (DSM ACC2118).

13. Monoclonal antibody AICD2.M2, which is specific for an epitope of antigen CD2, and is obtainable by isolation from hybridoma cell line 7 D 3 (DSM ACC2119).

14. A pharmaceutical formulation comprising a bispecific antibody fragment of claim 1, and a pharmaceutically acceptable excipient.

15. A kit comprising a first pharmaceutical formulation (I) of claim 14, wherein the bispecific antibody fragment is BAb<X, AICD2.M2>Y and a second pharmaceutical formulation (II) comprising MAb.AICD2.M1, or MAb<AICD2.M1>Y, or BAb<X, AICD2.M1>Y, wherein X and Y have the indicated meanings, together with a pharmaceutically acceptable excipient.

16. A kit comprising a first pharmaceutical formulation (I) of claim 14, wherein the bispecific antibody fragment is BAb<X, AICD2.M1>Y and a second pharmaceutical formulation (II) comprising MAb.AICD2.M2, or MAb<AICD2.M2>Y, or BAb<X.AICD2.M2>Y, wherein X and Y have the indicated meanings, together with a pharmaceutically acceptable excipient.

17. A kit of claim 16, wherein formulation (1) comprises a bispecific antibody fragment selected from Bab<425,AICD2.M1>F(ab')$_2$ or BAb<361,AICD2.M1>F(ab')$_2$, and formulation (II) comprises MAb<AICD2.M2>F(ab')$_2$.

* * * * *